United States Patent [19]
Collis et al.

[11] Patent Number: 5,707,860
[45] Date of Patent: Jan. 13, 1998

[54] VEHICLE FOR DELIVERY OF PARTICLES TO A SAMPLE

[75] Inventors: Matthew P. Collis, Seven Valleys, Pa.; Allen S. Reichler, Owing Mills, Md.

[73] Assignee: Becton Dickinson and Company, Franklin Lakes, N.J.

[21] Appl. No.: 614,230

[22] Filed: Mar. 12, 1996

[51] Int. Cl.$^6$ ........................................... C12M 3/00
[52] U.S. Cl. ................................. 435/287.2; 435/288.1; 435/306.1; 436/177
[58] Field of Search .................... 436/523, 525, 436/527, 177, 178; 435/30, 287.2, 287.6, 288.1, 306.1

[56] References Cited

U.S. PATENT DOCUMENTS

| | | | |
|---|---|---|---|
| 4,666,850 | 5/1987 | Mehl et al. | 435/243 |
| 5,376,527 | 12/1994 | Robson et al. | 435/6 |
| 5,464,773 | 11/1995 | Melendez et al. | 435/306.1 |

*Primary Examiner*—David A. Redding
*Attorney, Agent, or Firm*—David W. Highet, Esq.

[57] ABSTRACT

The present invention relates to a vehicle for delivery of particles to a sample of cells. The vehicle includes a barrier to retain the particles, which barrier in one embodiment is a frangible, dissolvable or meltable material. Once released into the sample, the particles are useful in methods to lyse or disrupt cells or in methods to separate cellular components from one another if the cells in the sample are already lysed or disrupted.

11 Claims, 4 Drawing Sheets

5,707,860

VEHICLE FOR DELIVERY OF PARTICLES TO A SAMPLE

BACKGROUND OF THE INVENTION

Access to cellular components such as nucleic acids is imperative to a variety of molecular biology methodologies. Such methodologies include nucleic acid sequencing, direct detection of particular nucleic acid sequences by nucleic acid hybridization and nucleic acid sequence amplification techniques.

Although access to nucleic acids from the cells of some organisms does not involve particularly complex methodologies or harsh treatments, other organisms have cells from which it is particularly difficult to access nucleic acids or other cellular components. Organisms in the latter group include species of the genus Mycobacteria, yeast and fungi. Usually, the difficulty in cellular component access is a result of organism cell walls which are highly resistant to lysis or disruption, and/or the adherence of certain cellular components such as nucleic acids to cellular proteins and other cellular substances such as pieces of cell walls.

Recently, a new method to access nucleic acids has been discovered which is more fully disclosed in a co-pending patent application Ser. No. 08/614,108, filed on even date herewith, the disclosure of which is expressly incorporated herein by reference. Briefly this new method to access nucleic acids involves subjecting a sample of disrupted cells to agitation in the presence of particles to separate nucleic acids from other cellular components. This method has been found to be particularly useful to access nucleic acids from the cells of mycobacterial organisms after those cells have been disrupted by the application of heat.

However, the addition of the particles to the sample of cells was found to present certain difficulties. Generally, the particles are scooped from a bulk quantity into the sample, and thus there tend to be inconsistent quantities of particles delivered to the sample. Also, the scooping and attempt to deliver as precise and consistent an amount of particles to the sample adds additional time to the overall process. Furthermore, in the attempt to deliver a precise amount of particles to the sample, the scoop delivering the particles is brought in close proximity to the opening of the sample container, and thus risks contamination of the scoop, and subsequent contamination of the bulk quantity of particles and all further samples to which particles are added. Moreover, occasionally, a particle becomes lodged at the opening of the sample container in such a manner that a proper seal can not be established. This would often result in sample loss, particularly if a heating step is involved in the process.

SUMMARY OF THE INVENTION

The present invention provides solutions to these difficulties encountered when adding particles to samples of cells by providing a vehicle with a barrier to retain the particles until the particles are released into the sample. The barrier may be of any nature which will cause release of the particles for use in agitation of the sample to disrupt cells and/or separate cellular components from one another. One embodiment of the vehicle is a capsule wherein a frangible, dissolvable or meltable surface or wall of the capsule is the barrier which retains the particles.

BRIEF DESCRIPTION OF THE DRAWINGS

The various objects, advantages and novel features of the invention will be more readily appreciated from the following detailed description when read in conjunction with the appended figures in which.

DETAILED DESCRIPTION OF THE INVENTION

In a broad aspect, the present invention provides a vehicle for delivering particles to a sample of cells. The vehicle includes a barrier which retains the particles until released into the sample.

Based on the desired objects of the invention, that is to deliver a precise, consistent quantity of uncontaminated particles to a sample of cells, the vehicle may be of a variety of forms. Suitable vehicles include some type of barrier to retain the particles until release into the sample.

For example, vehicles may have physical barriers to retain the particles, and thus take the form of receptacles such as vessels, capsules, sacks, pods, pouches and other containers and carriers. Alternatively, the vehicles may have other physical barriers, which rather than surrounding the particles to retain them, are on the particles such as dissolvable glues such as trehalose, pastes, mortars or other adhesives. Yet another embodiment is a vehicle for which the barrier is a nonphysical means for retaining the particles as a unit prior to release into the sample such as electrostatic forces.

Figure 7:
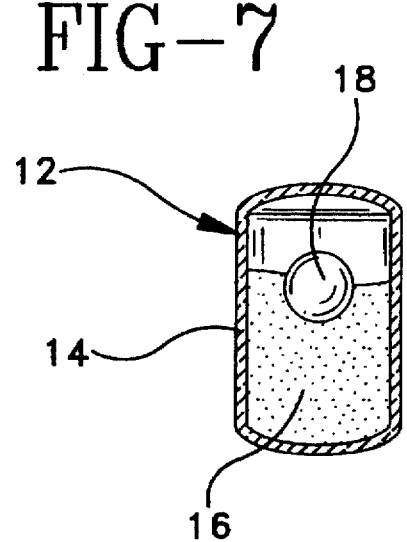
FIG. 7 is an enlarged cross-sectional view of the vehicle.

One example of a suitable vehicle is illustrated in FIG. 7 which shows a capsule 12. In this embodiment, the barrier is the surface or wall 14 of the capsule.

In such an embodiment, the barrier may be made of any material which can be designed to retain the particles 16 until their desired release into a sample. For example, such a barrier may be made of a frangible, dissolvable or meltable material. Also, a portion of the barrier may be frangible, dissolvable or meltable whereas the remainder of the barrier is not so, such that particle release occurs from only a portion of the vehicle.

In the case of a dissolvable barrier material, the material is selected based on the nature of the sample and the desired time of release of the particles. Gelatin, polyethylene glycol (PEG) and certain sugar materials, for example, may generally be customized by inclusion of particular constituents to dissolve at faster or slower rates.

Also, a portion of the barrier may be frangible, dissolvable or meltable whereas the remainder of the barrier is not so, such that particle release occurs from only a portion of the vehicle.

With a meltable barrier material, the material need merely be selected based on its melting profile (temperature and time or rate). For example, when used in a sample processing method that includes a heating step to render infectious organisms noninfectious and/or disrupt cells, a barrier material which melts at temperatures greater than about 80° C. is suitable as most such heating steps apply temperatures of at least 80° C. to the sample.

Frangible barrier materials include any materials which will break due to impact of a particle therewith, impact of the frangible barrier material with a sample container or upon centrifugation which causes sufficient force to be applied to particles against the frangible barrier. Suitable frangible materials include onion skin glass, carbowax, stiff plastics such as cellophane, certain laminates, plastic coated foils, or any frangible organic compound which will not immediately dissolve in a sample and is compatible with later processing of the sample.

In one embodiment of the vehicle 12 shown in FIG. 7 wherein the barrier 14 is a frangible material, at least one particle of greater size than the other particles 16, a so-called "breaker particle" 18, is included in the vehicle. The breaker particle is of sufficient size to cause breaking of the barrier 14 upon impact caused by agitation of the sample. Thus, the breaker particle 18 contributes to the initial breaking of a frangible barrier 14, and also contributes to subsequent breaking of pieces of the barrier as the particles 16 are released into the sample and move therethrough.

The particles, including the breaker particle may be of various compositions including for example, glass, plastic, sand silicates, latex, crystals, metals such as zirconium, metal oxides, etc. Due to the use of the particles in an agitation process to disrupt cells or to separate cellular components from one another in a sample of disrupted cells, the particles preferably remain undissolved in the sample for a time sufficient to complete the agitation process. Although non-dissolvable particles are preferred, a particle with a slow rate of dissolution would also be suitable.

The particles may also be of various shapes, including for example, spheres, cubes, oval, capsule-shaped, tablet-shaped, non-descript random shapes, etc., and may be of uniform shape or non-uniform shapes. Whatever the shape of a particle, its diameter at its widest point is generally in the range of from about 0.1 mm to about 0.15 mm. Particles with diameters greater than about 0.5 mm have been found to be not as effective in separating cellular components from one another.

In contrast, the breaker particle generally has a diameter at its widest point of at least about 1 mm, and may have a widest point diameter up to about 4 mm. When using zirconium particles with widest point diameters of about 0.1 mm, a useful breaker particle is a glass particle with a widest point diameter of about 3 mm. Thus, this breaker particle is of greater size than the zirconium particles which, after release from the vehicle, shear cellular components from one another during agitation of the sample of disrupted cells.

The amount of particles retained in the vehicle is dependent upon the amount of and viscosity of the sample to which the vehicle is added. Generally, a typical clinical sample from which a clinician would desire to access nucleic acids for diagnostic purposes has a volume of about 1 mL or less. However, other samples such as environmental samples or food product samples may have greater volumes, and other samples may have lesser volumes.

It has been found that the amount of headspace between the volume of particles 16 in a vehicle 12 and the barrier 14 makes very little difference in the ability of the vehicle 12 to deliver particles 16 to the sample. This lack of a specific headspace requirement is found with frangible, dissolvable and meltable barriers.

The viscosity of different samples may vary. For example, within the category of clinical samples, a sputum sample is generally more viscous than a blood or urine sample. Similarly, the viscosities of different environmental samples will also vary.

As a general rule, in viscous samples such as sputum, the volume of particles added to a given volume of sample will be in a ratio of about 0.25:1 to about 1:1. With less viscous samples, a lesser volume to volume ratio of particles to sample is believed to be sufficient to access nucleic acids from the sample.

The vehicle of the present invention can be used to deliver particles to a sample for a variety of purposes. However, commonly, the vehicle will deliver particles to a sample of cells for a cell disruption or lysis process including agitation or sonication of the sample. Such cell lysis or disruption processes are well known to those skilled in the art from references such as Hurley, S. S. et al., *J. Clin. Microbiol.* 25 (11) 2227–2229 (1987) which describes the agitation of samples of mycobacterial cells with beads and the lysogenic agent, phenol, in a Biospec Mini-Beadbeater instrument and Shah, J. S. et al., *J. Clin. Microbiol.* 33 (2) 322–328 (1995) which describes the agitation of samples of *M. tuberculosis* cells with beads and the lysogenic agent, guanidium thiocyanate (GuSCN), in a GENE-TRAK Sample Processing instrument.

Another use of the vehicle of the present invention is to deliver particles to a sample of cells which have already been lysed or disrupted. It has been found that agitation of such a sample of disrupted cells with particles provides optimal yields of accessible nucleic acids due to separation or shearing of the nucleic acids from other cellular components such as proteins and cell wall fragments. Such a method for accessing nucleic acids from disrupted cells is taught in greater detail in co-pending U.S. patent application Ser. No. 08/614,108, filed on even date herewith the disclosure of which is expressly incorporated herein by reference.

Figure 1:
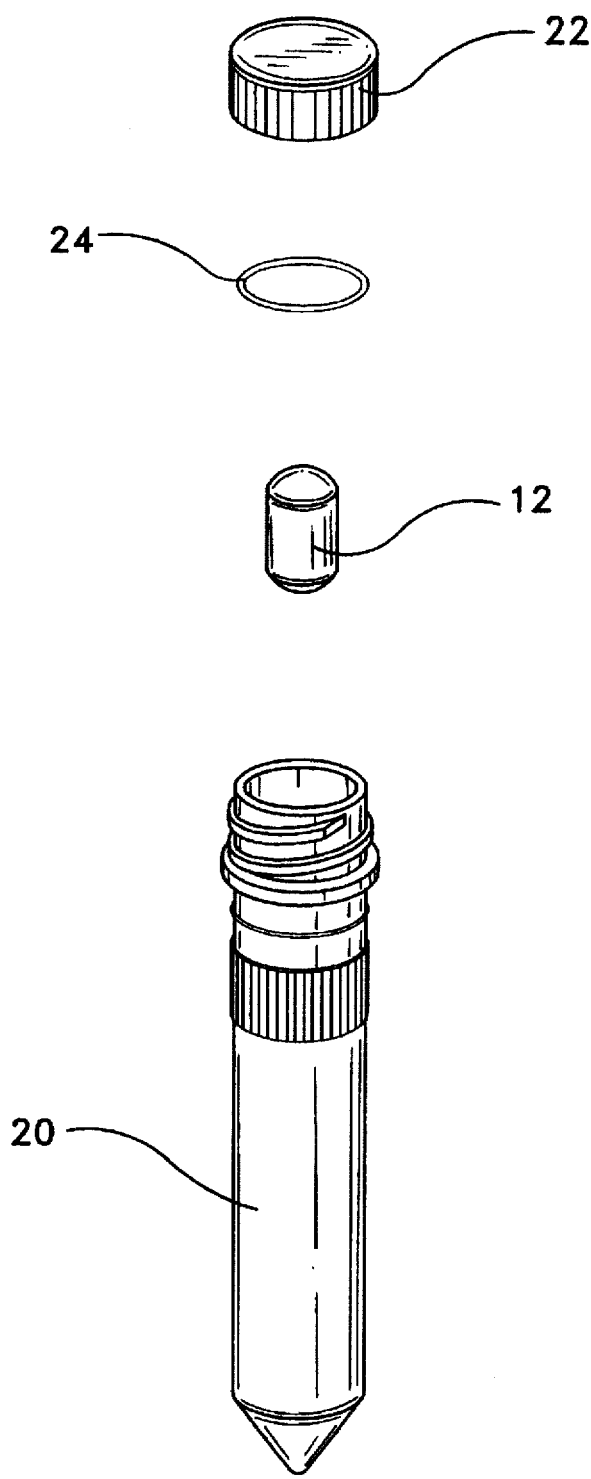
FIG. 1 is an exploded perspective view of one embodiment of the vehicle of the present invention and a typical screw cap sample tube into which the vehicle would be placed.

Samples of cells, whether disrupted or not, are typically contained in a sample tube 20 such as that shown in FIG. 1. In order to avoid loss of sample during agitation or other manipulations, such tubes generally have a screw-cap 22 and a gasket (o-ring) 24 to aid in providing a tight seal between the top of the sample tube and the screw-cap.

Figure 2:
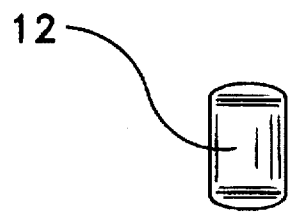
FIG. 2 is an exploded cross-sectional view of the vehicle and sample tube of FIG. 1.
Figure 2:
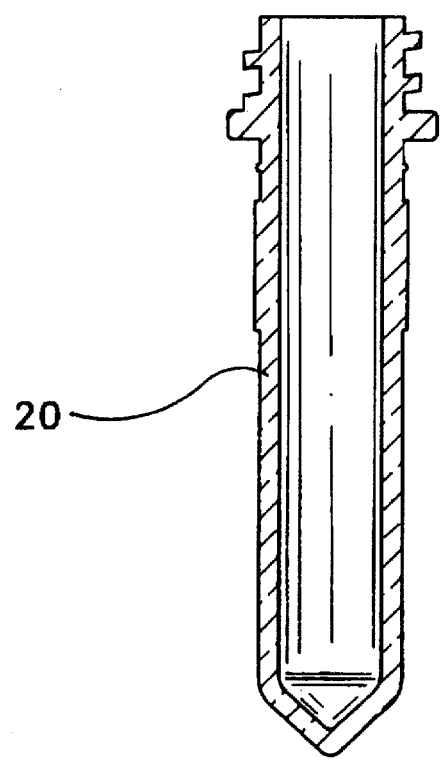
Figure 3:
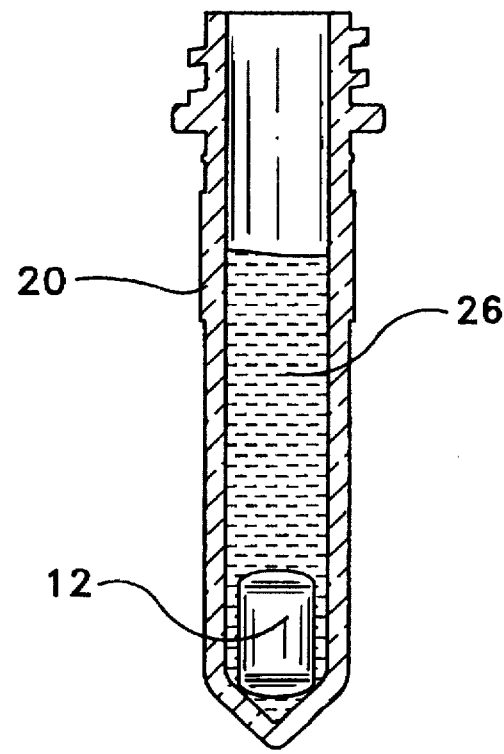
FIG. 3 is a cross-sectional view of the vehicle in a sample in the sample tube.

As shown in FIG. 2 and FIG. 3, the vehicle 12 is placed into the sample tube 20 either before or after a sample 26 is added. As stated above, the sample 26 may be of intact, non-disrupted cells or of disrupted cells or a combination of both. As shown in FIG. 3, the vehicle will generally settle at the bottom of the sample in the tube.

Figure 4:
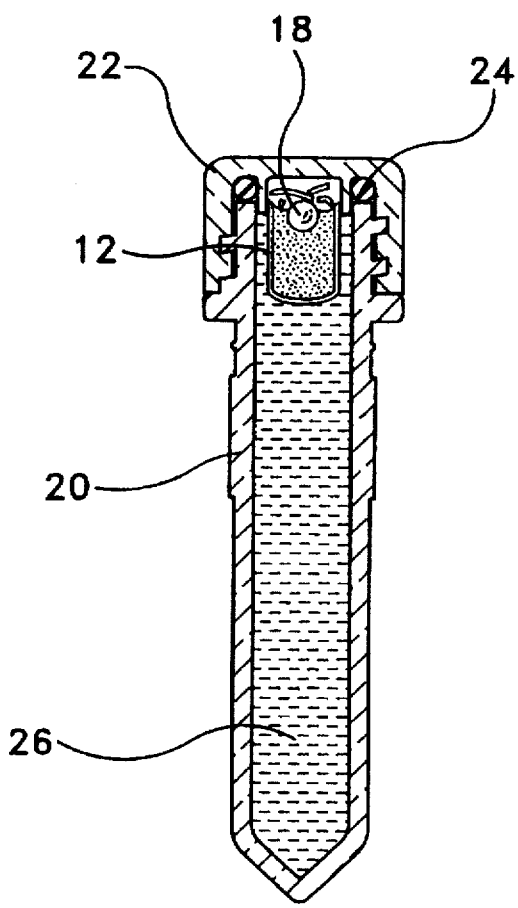
FIG. 4 is a cross-sectional view showing the initial release of particles from the vehicle in the sealed sample tube during agitation.

Once the sample tube 20 has been capped, as shown in FIG. 4, the tube may be agitated which causes the sample 26 and the vehicle 12 to move throughout the tube. As the vehicle moves through the sample, and particularly when the vehicle contacts an interior wall of the tube, the impact of the breaker particle 18 against the vehicle barrier 14 causes the barrier to break.

Figure 5:
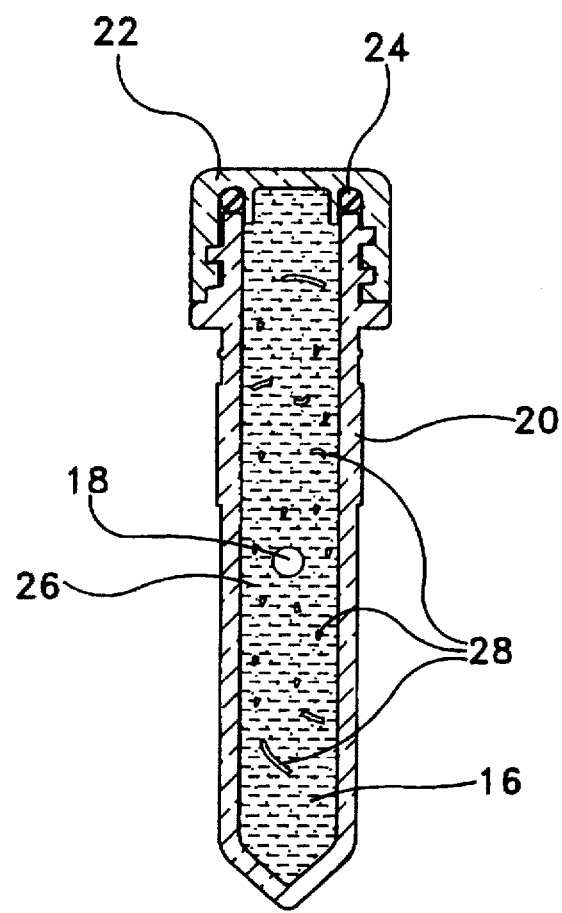
FIG. 5 is a cross-sectional view of released particles in the sealed sample tube during agitation.
Figure 6:
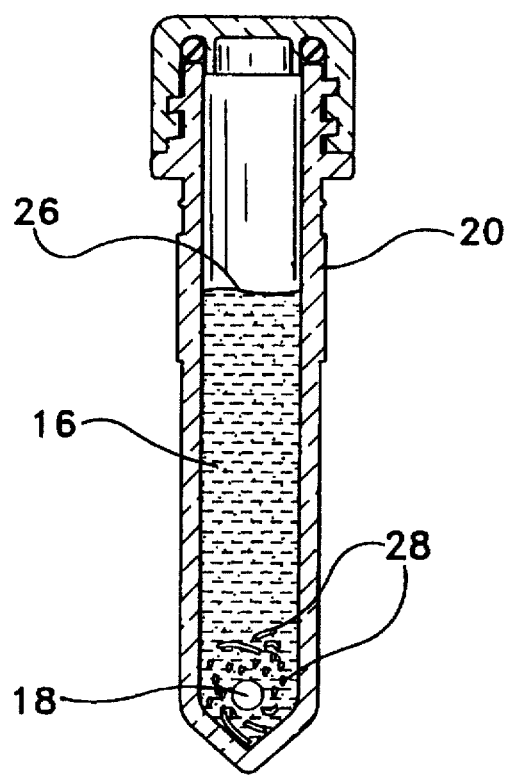
FIG. 6 is a cross-sectional view of released particles in the sealed sample tube after agitation is completed.

The breaking of the barrier 14 permits the release of particles 16 from the vehicle 12 into the sample 26 as shown in FIG. 5. Thus, during agitation and after release of particles from the vehicle, particles 16, breaker particle 18 and fragments 28 of the vehicle barrier are distributed throughout the sample 26. Following the completion of agitation of the sample, the particles 16, breaker particle 18 and vehicle barrier fragments 28 settle to the bottom of the sample 26, thus permitting removal of the sample from the tube by pipetting or other similar means without interference from the particles, breaker particle or vehicle barrier fragments.

The following examples illustrate specific embodiments of the invention described in this document. As would be apparent to skilled artisans, various changes and modifications are possible and are contemplated within the scope of the invention described.

EXAMPLE 1

Preparation of Vehicles With a Frangible Barrier

Preparation of Zirconium Capsules

This experiment was performed to prepare a vehicle to deliver particles to a sample which has a barrier sufficiently frangible to disrupt in Lab craft® tubes when agitated in a BioSpec bead beater.

Materials

The materials used in this experiment were:

Borosilicate Glass 6.9 mm in diameter

Zirconium/Silicate beads (0.1 mm to 0.15 mm diameter) Cole Palmer Cat. #36270-62

3.0 mm Glass Breaker Bead Curtin Matheson Cat. #125-021

Labcraft® 2.0 ml capacity conical bottom microfuge tubes Catalog #273-695

Procedure

Borosilicate glass at 6.9 mm in diameter was sealed on one end on a Fletcher-Terry glass sealing instrument. Zirconium/silicate particles (0.1 mm to 0.15 mm) were dispensed into each sealed glass piece at 2.2 gms to 2.3 gms/piece. The piece containing zirconium/silicate particles was sealed at 3.0 cm total length to form the vehicle. A glass breaker particle (3.0 mm diameter) was inserted into each of five 2.0 ml conical Labcraft® tubes. One vehicle was inserted into each tube and 1.0 ml of water was dispensed into the tube. The tubes containing capsules, beads and water were inserted into a BioSpec® bead beater. The tubes were agitated at 2,600 RPM for 1.0 minute.

Results

All capsules in the Labcraft tubes® were disrupted by agitation in the BioSpec bead beater.

Conclusion

Vehicles containing a sufficient volume of particles for delivery to a typical sample volume were produceable. In addition, the vehicles disrupted within the Labcraft® tubes as desired and released the particles.

EXAMPLE 2

Determination of Volume of Particles for Inclusion in Vehicles

This experiment was performed to determine whether varying the volume of particles in a vehicle affects the recovery and detection of target nucleic acid from a sample.

Materials

The following materials were used in this experiment.

KPDG Lot #95-01B

Negative NALC Pellet Pool 0.1 mm Zirconium/Silicate beads Cole Palmer Catalog #36270-62

Glass 3.0 mm Breaker bead Curtin Matheson Catalog #125-021

Zirconium Capsules 3.0 cm Lot #0161-33

*Mycobacterium tuberculosis* H37Rv Particles Lot #081095DS

Pre-amplification buffer Lot #95-02A

Pre-decontamination buffer Lot #95-01A

Amplification buffer Lot #95-471

Decontamination buffer Lot #95-472

LumiPhos 530 Lot #052695

Mtb hybridization mix Lot #95-01B

Genus hybridization mix Lot #95-02

Signature hybridization mix Lot #95-01

System Fluid Lot #95-03A

Stringency Wash Lot #95-03A

AD plates Lot #95-03

Labcraft® tubes Catalog #273-695

Procedure

*M. tuberculosis* H37R cells were washed with M/15 Phosphate buffer to remove any extracellular DNA. The cells were resuspended in the phosphate buffer, enumerated and diluted (in phosphate buffer) to working concentrations.

Using one of the working concentrations, Mtb particles were spiked into Negative NALC sediment for a final concentration of the Mtb particles in the Negative NALC sediment of 500 particles/0.25 ml. The spiked Negative NALC sediment was transferred to 2.0 ml conical Labcraft® tubes at 0.25 ml/tube.

One milliliter of KPDG was added to each tube and the tubes were centrifuged at 12,000 g for 3.0 minutes. The supernate was decanted from each tube and 1.0 ml of KPDG was added to each tube. The tubes were centrifuged at 12,000 g for 3.0 minutes. The supernate was decanted.

One ml of 0.1 mm zirconium/silicate beads and then 1.0 ml of KPDG was added to 24 of the above-described tubes containing washed H37R cells. Two sets (eight tubes/set) of these tubes containing 1.0 ml of 0.1 mm zirconium beads and KPDG were heated in a forced hot air oven and then agitated using a BioSpec® beadbeater at 2,600 RPM for 2.0 minutes and the other set of tubes was not agitated.

A 3.0 mm glass breaker particle, a vehicle containing 1.0 ml of zirconium particles as described in Example 1 and then 1.0 ml of KPDG was added to eight tubes containing washed H37R cells. This set of tubes containing a breaker bead, a particle containing vehicle and KPDG were agitated at 2600 RPM for 2.0 minutes using the BioSpec® bead beater.

Seven hundred and fifty microliters of 0.1 mm zirconium particles and then 1.0 ml of KPDG were added to eight tubes containing washed H37R cells. This set of tubes containing 750 ul of zirconium particles was heated in a forced hot air oven for 30 minutes at 105° C. and then agitated for 2.0 minutes at 2,600 RPM.

Two other sets of H37R cells containing tubes containing 500 microliters and 250 microliters of 0.1 mm zirconium particles respectively, were treated in the same manner.

One milliliter of KPDG was added to the remaining sixteen tubes containing washed H37R cells. One set of tubes was heated in a forced hot air oven for 30 minutes at 105° C. and then agitated at 2,600 RPM for 2.0 minutes using the BioSpec® bead beater, and the remaining set of tubes was heated in a forced hot air oven but not agitated.

Strand Displacement Amplification (SDA) and detection procedures described in Example 1 of copending U.S. patent application Ser. No. 08/614,108, filed on even date herewith, expressly incorporated herein by reference were performed on all tubes of this Example. More specifically, a 30 μl aliquot of each sample ("undiluted sample") was run directly in an SDA assay with the following reagents under the following conditions:

The 30 ul sample was combined with 5 ul of Pre-Amp Buffer in a 0.5 mL microcentrifuge tube. This sample was heated for 3 minutes in a boiling water bath. To this was added 10 ul of the Decontamination Drydown Mix and an amplicon decontamination reaction was conducted for 50 minutes at 41° C. Amplicon decontamination was conducted using a method well known to those skilled in the art from references such as U.S. Pat. No. 5,035,996, the disclosure of which is expressly incorporated herein by reference. Briefly, during a nucleic acid amplification process, the nucleotide dUTP is substituted for dTTP, and thus all products which are replicated from the target DNA sequence (amplicons) contain dUTP instead of dTTP. Then, prior to a nucleic acid amplification process, the sample is contacted with the enzyme uracil DNA glycosylase (UDG). The UDG cleaves the glycosidic bond between uracil and the sugar deoxyribose when dUTP is incorporated into a DNA molecule. Thus, amplicons from previous nucleic acid amplification processes are rendered non-amplifiable (i.e. are not suitable as templates for replication). Therefore, only true target sequence in the sample will serve as template for nucleic acid amplification.

Following amplicon decontamination, 10 ul of the Amplification Drydown Mix was added and the sample incubated for another 2 hours at 41° C. to permit Strand Displacement Amplification (SDA) process to proceed. SDA is a nucleic acid amplification process well known to those skilled in the art. Briefly, Strand Displacement Amplification (SDA) is an isothermal method of nucleic acid amplification in which extension of primers, nicking of a hemimodified restriction endonuclease recognition/cleavage site, displacement of single stranded extension products, annealing of primers to the extension products (or the original target sequence) and subsequent extension of the primers occur concurrently in the reaction mix. This is in contrast to the PCR, in which the steps of the reaction occur in discrete phases or cycles as a result of the temperature cycling characteristics of the reaction. SDA is based upon 1) the ability of a restriction endonuclease to nick the unmodified strand of a hemiphosphorothioate form of its double stranded recognition/cleavage site and 2) the ability of certain polymerases to initiate replication at the nick and displace the downstream non-template strand. After an initial incubation at increased temperature (about 95° C.) to denature double stranded target sequences for annealing of the primers, subsequent polymerization and displacement of newly synthesized strands takes place at a constant temperature. Production of each new copy of the target sequence consists of five steps: 1) binding of amplification primers to an original target sequence or a displaced single-stranded extension product previously polymerized, 2) extension of the primers by a 5'-3' exonuclease deficient polymerase incorporating an α-thio deoxynucleoside triphosphate (αthio dNTP), 3) nicking of a hemimodified double stranded restriction site, 4) dissociation of the restriction enzyme from the nick site, and 5) extension from the 3' end of the nick by the 5'-3' exonuclease deficient polymerase with displacement of the downstream newly synthesized strand. Nicking, polymerization and displacement occur concurrently and continuously at a constant temperature because extension from the nick regenerates another nickable restriction site. When a pair of amplification primers is used, each of which hybridizes to one of the two strands of a double stranded target sequence, amplification is exponential. This is because the sense and antisense strands serve as templates for the opposite primer in subsequent rounds of amplification. When a single amplification primer is used, amplification is linear because only one strand serves as a template for primer extension. Examples of restriction endonucleases which nick their double stranded recognition/cleavage sites when an α-thio dNTP is incorporated are HincII, HindII, AvaI, NciI and Fnu4HI. All of these restriction endonucleases and others which display the required nicking activity are suitable for use in conventional SDA. However, they are relatively thermolabile and lose activity above about 40° C.

Targets for amplification by SDA may be prepared by fragmenting larger nucleic acids by restriction with an endonuclease which does not cut the target sequence. However, it is generally preferred that target nucleic acids having the selected restriction endonuclease recognition/cleavage sites for nicking in the SDA reaction be generated as described by Walker, et al. 1992. *Proc. Natl. Acad. Sci USA* 89, 392–396, Walker, et al. 1992. *Nucl. Acids Res.* 20, 1691–1696 and in U.S. Pat. No. 5,270,184 (hereby expressly incorporated by reference). Briefly, if the target sequence is double stranded, four primers are hybridized to it. Two of the primers ($S_1$ and $S_2$) are SDA amplification primers and two ($B_1$ and $B_2$) are external or bumper primers. $S_1$ and $S_2$ bind to opposite strands of double stranded nucleic acids flanking the target sequence. $B_1$ and $B_2$ bind to the target sequence 5' (i.e., upstream) of $S_1$ and $S_2$, respectively. The exonuclease deficient polymerase is then used to simultaneously extend all four primers in the presence of three deoxynucleoside triphosphates and at least one modified deoxynucleoside triphosphate (e.g., 2'-deoxyadenosine 5'-O-(1-thiotriphosphate), "dATPαS"). The extension products of $S_1$ and $S_2$ are thereby displaced from the original target sequence template by extension of $B_1$ and $B_2$. The displaced, single stranded extension products of the amplification primers serve as a targets for binding of the opposite amplification and bumper primer (e.g., the extension product of $S_1$ binds $S_2$ and $B_2$). The next cycle of extension and diplacement results in two double stranded nucleic acid fragments with hemimodified restriction endonuclease recognition/cleavage sites at each end. These are suitable substrates for amplification by SDA. As in SDA, the individual steps of the target generation reaction occur concurrently and continuously, generating target sequences with the recognition/cleavage sequences at the ends required for nicking by the restriction enzyme in SDA. As all of the components of the SDA reaction are already present in the target generation reaction, target sequences generated automatically and continuously enter the SDA cycle and are amplified.

The SDA reaction originally reported in the publications cited above ("conventional SDA") is typically conducted at a temperature between about 35° C. and 45° C., and is capable of $10^8$-fold amplification of a target sequence in about 2 hours. Recently, SDA has been adapted for higher reaction temperatures (about 45°–65° C.—"thermophilic SDA" or "tSDA"). tSDA is capable of producing $10^9$–$10^{10}$ fold amplification in about 15–30 min. at about 50°–60° C. In addition to increased reaction speed, there is a significant reduction in non-specific background amplification in tSDA as compared to conventional SDA.

Detection of amplified target Mycobacterium genus sequence and *M. tuberculosis* complex species sequence (IS6110) was conducted in an assay only format on the BDProbeTec™ instrument. This detection system is fully described by C. A. Spargo et al. in *Molec. Cellular Probes* 7:395–404 (1993).

The BDProbeTec™ instrument is an automated system for performing SDA assays. The particular details of embodiments of the BDProbeTec™ instrument which was used to automatically perform the detection of amplified target sequences after SDA assays in this Example are disclosed in U.S. patent application Ser. No. 08/409,821, filed Mar. 24, 1995, the disclosure of which is expressly incorporated herein by reference.

Results:

The results of this Example are set forth in Table 1 below.

TABLE 1

| Particle Type | Agitate | Mean Mtb RLUs | Mean Genus RLUs |
|---|---|---|---|
| 1.0 ml of particles(*) | Yes | 149.9 | 42.5 |
| 750 ul of particles | Yes | 131.8 | 43.0 |
| 500 ul of particles | Yes | 160.6 | 43.6 |
| 250 ul of particles | Yes | 141.2 | 55.2 |
| Breaker particles and Vehicle | Yes | 188.8 | 59.4 |
| None | Yes | 7.3 | 6.5 |
| None | No | 4.2 | 3.2 |
| 1.0 ml of particles | No | 6.2 | 1.8 |

(*)Four samples were lost due to insufficient fluid volume post heating.

Conclusion:

Processed samples showed statistically equivalent results for all four particle volumes (1.0 ml, 750 ul, 500 ul and 250 ul). Use of vehicles showed statistically equivalent results to the loose particle volume results. Loose particle and particle containing vehicle results were statistically better for Mtb and Genus detection than for samples containing no particles or for those samples which were not agitated.

Four samples were lost in the one set containing one ml of loose zirconium particles. It is believed that these samples were lost due to particles rimming the top of the rubber gasket on the Labcraft® tubes, producing an air gap which allowed the loss of sample during heating.

EXAMPLE 3

Agitation of Particle Containing Vehicles in Samples

This experiment was designed to produce vehicles of varying lengths, containing varying volumes of particles with and without a 3.0 mm glass breaker particle. The vehicles were evaluated based on disruption in a Savant FastPrep™ instrument.

Materials

Borosilicate Glass 6.9 mm diameter stock 0.1 mm Zirconium/silicate beads Lot #072795

3.0 mm Sodium Silicate Glass Beads Curtin Matheson Catalog #125-021

Labcraft® tubes Catalog #273-695

Procedure

Flat bottomed 6.9 mm diameter glass stock was prepared at a length of 4.5 cm. A Mark-10 EG50 force meter was used to determine that <10 pounds of force was required to break the dome on 10 of these pieces.

Then, a 0.56 gm (250 ul) aliquot of zirconium/silicate particles was dispensed into bottom sealed glass pieces. A Cozzoli capping instrument was adjusted to prepare vehicles of 1.0 cm, 1.5 cm, 2.0 cm and 2.5 cm lengths. Force measurements were performed on these vehicles and it was determined that <10 lbs of force was required to disrupt the dome on these vehicles as well.

All vehicles were then evaluated for disruption with a Savant FastPrep™ instrument. The vehicles were inserted into Labcraft® tubes and 1.0 ml of water was dispensed into each tube. The tubes were inserted into the FastPrep™ instrument in sets based on vehicle length and whether the vehicle contained a 3.0 mm breaker particle.

The FastPrep™ instrument velocity setting was adjusted to 5.5 meters/second and the time setting was adjusted to 45 seconds. The FastPrep™ instrument was then activated and the number of capsules disrupted per type was recorded.

Results:

The results of the above procedure are set forth in Table 2 below.

TABLE 2

| VEHICLE TYPE | NO. OF DISRUPTIONS | NO OF VEHICLES TESTED |
|---|---|---|
| 2.5 cm without 3.0 mm particle(*) | 3 | 3 |
| 2.0 cm without 3.0 mm particle | 9 | 10 |
| 1.5 cm without 3.0 mm particle | 10 | 10 |
| 1.0 cm without 3.0 mm particle | 10 | 10 |
| 2.5 cm with 3.0 mm particle | 10 | 10 |
| 2.0 cm with 3.0 mm particle | 10 | 10 |
| 1.5 cm with 3.0 mm particle | 10 | 10 |
| 1.0 cm with 3.0 mm particle | 9 | 9 |

(*)A set of this type was evaluated at a higher velocity setting of 6.5 meters/second and produced excessive stress on the cap, with resulting loss of sample.

Conclusion

Based on the results from this experiment, all of the vehicles containing the 3.0 mm breaker particle were considered acceptable. The vehicles which did not contain the breaker particle had one disruption failure at a longer length of 2.0 cm. Therefore, in order to minimize splashing of the KPDG during addition of the vehicle and minimize the amount of barrier material used, the shorter vehicles (the 1.0 cm vehicles with and without 3.0 mm breaker particles) were evaluated further for both disruption and functionality.

EXAMPLE 4

Optimization of Vehicle Length

This experiment was performed to evaluate the use of 1.0 cm length vehicles (with and without a 3.0 mm breaker particle), the use of two 1.0 cm vehicles with 3.0 mm breaker particle (two vehicles/sample tube) and 1.0 ml of free zirconium particles, for disruption (in the case of vehicles) and for detection of target nucleic acid from a sample of disrupted cells.

Materials

The materials used in this Example were:

0.1 mm free Zirconium beads Cole Palmer Catalog #36270-62

1.0 cm length glass vehicles with 3.0 mm glass bead Lot #092295

1.0 cm length glass vehicles without 3.0 mm glass bead Lot #092295

KPDG Lot #95-A

Negative NALC sediment Lot #081695

Mtb H37Rv Lot #092895DS Stock concentration

Labcraft® tubes Catalog #273-695

Pre-amplification buffer Lot #95-02A

Pre-decontamination buffer Lot #95-01A

Decontamination mix Lot #95-605

Amplification mix Lot #95-604

Mtb Hybridization mix Lot #95-02

Genus Hybridization mix Lot #95-451A and 95-451B

Signature Hybridization mix Lot #95-02

LumiPhos 530 Lot #052695

AD Lot #95-05
Stringency wash Lot #063095
System Fluid Lot #95-03A

Procedure

Negative NALC sediment was spiked to final concentrations of 2000 particles of H37Rv/ml and 800 particles of H37Rv using washed cellular stock concentrations of H37Rv from Example 2. Each concentration of spiked NALC solution was transferred to fifty tubes/solution at 250 ul/tube.

One milliliter of KPDG was added to each tube and the tubes were centrifuged at 12,000 g for 3.0 minutes. The supernate was decanted from each tube and 1.0 ml of KPDG was added to each tube. The tubes were centrifuged again at 12,000 g for 3.0 minutes and the supernate was decanted.

Two 1.0 cm length vehicles (with 3.0 mm breaker particle) were added to ten tubes at each concentration and then one ml of KPDG was added to each tube. One 1.0 cm length vehicle (with 3.0 mm breaker particle) was added to ten tubes at each concentration and then one ml of KPDG was added to each tube. One 1.0 cm length vehicle (without 3.0 mm breaker particle) was added to twenty tubes at each concentration and then one ml of KPDG was added to each tube. One ml of zirconium/silicate particles were added to ten tubes at each concentration and then one ml of KPDG was added to each tube.

The tubes were heated in a forced hot air oven at 105° C. for 30 minutes. The tubes were then agitated in a Savant FastPrep™ instrument at a setting 5.0 m/s for 45 seconds.

Strand Displacement Amplification (SDA) and detection procedures were performed as described in Example 2 to generate the results from this experiment in Relative Light Units (RLUs).

Results

The results of this Example are set forth below in Table 3.

Materials

The materials used in this experiment were:
Sample Diluent (KPDG) Part #360691
Gelatin Capsules NOW™ Code #5215 Type #3
Zirconium Beads (0.1 mm–0.15 mm) Biospec Catalog #110791O1Z Procedure Zirconium beads were dispensed into four gelatin capsules at 0.56 gms/capsule. The capsules were inserted into Labcraft® tubes at one capsule/tube and 1.0 m. of sample diluent was dispensed into each tube. The tubes were capped and the tubes were inserted into a forced hot air oven. The tubes were maintained in the forced hot air oven at 105° C. for 30 minutes. The tubes were removed from the oven after the tubes had cooled to 40° C. The tubes were transferred to a Savant Fast Prep™ instrument. The velocity setting was adjusted to 5.0 m/s and the time was adjusted to 45 seconds. The FastPrep™ instrument was activated and results were recorded.

Results

The capsules solubilized or dissolved in the aqueous sample diluent in less than 20 minutes at 105° C. releasing the zirconium beads to the sample tube. No loss of sample fluid was recorded. The zirconium beads were free flowing in the sample tube at the point of agitation and immediately following agitation.

Conclusion

This experiment indicates that dissolvable capsules can be used as a delivery vehicle for the non-dissolvable particles to a sample. The gel capsule as with the glass capsule prevented free zirconium beads from disrupting the seal on the sample tube and cause the associated sample fluid loss. The zirconium beads were free flowing prior to and immediately after bead beating allowing the beads to disrupt bacterial cells and release DNA for amplification and detection reactions.

TABLE 3

| Particle Type Signature | M. tb. Particles/ | Mean Mtb Value | Mean Genus Values | Mean Values |
| --- | --- | --- | --- | --- |
| Two vehicles with 3.0 mm breaker particle | 500 | 155.2 | 30.8 | 114.4 |
| One vehicle with 3.0 mm breaker particle | 500 | 155.3 | 43.3 | 102.9 |
| One vehicle without breaker particle (3) | 500 | 154.9 | 31.5 | 69.4 |
| 1.0 ml free zirconium particles | 500 | 197.9 | 41.6 | 87.1 |
| Two vehicles with 3.0 mm breaker particle | 200 | 70.1 | 19.8 | 56.8 |
| One vehicle with 3.0 mm breaker particle | 200 | 61.4 | 23.8 | 124.2 |
| One vehicle without breaker particle (6) | 200 | 40.6 | 10.6 | 83.3 |
| 1.0 ml free zirconium particles | 200 | 71.0 | 14.8 | 83.3 |

( ) Capsules not disrupted

Conclusion

No statistical differences were seen for any of the conditions, illustrating the equivalence of the vehicle containing the breaker particle to 1.0 ml of free zirconium particles (the control) for effective Mycobacterium DNA presentation for nucleic acid amplification processes. The vehicle containing no breaker particle had 9/40 disruption failures making it unattractive for continued evaluation.

EXAMPLE 5

Evaluation of Dissolvable Vehicles

This experiment was performed to evaluate the use of dissolvable gelatin capsules as a delivery vehicle for zirconium particles.

While the invention has been described with some specificity, modifications apparent to those with ordinary skill in the art may be made without departing from the scope of the invention. Various features of the invention are set forth in the following claims.

That which is claimed is:

1. A vehicle for delivery of particles to a sample containing cells comprising a barrier which retains the particles until said particles are released into the sample, said particles being sufficiently non-dissolvable to remain undissolved in the sample for a time sufficient to disrupt the cells and render accessible nucleic acids therefrom when the sample is agitated or sonicated.

2. The vehicle of claim 1 wherein the barrier comprises a frangible material which releases the particles after breaking.

3. The vehicle of claim 2 wherein at least one particle is of sufficient size to cause the breaking of the barrier and the remainder of the particles are of a lesser size.

4. The vehicle of claim 1 wherein the particles are glass beads.

5. The vehicle of claim 1 wherein the particles are zirconium/silicate beads.

6. The vehicle of claim 3 wherein said at least one particle is a glass bead and the remainder of the particles are zirconium/silicate beads.

7. The vehicle of claim 1 wherein the barrier comprises a material which dissolves when contacted with the sample.

8. The vehicle of claim 1 wherein the barrier comprises a material which melts at a temperature greater than about 80° C.

9. A method for rendering cellular components accessible comprising the steps of:

(a) adding to a sample containing cells, the vehicle of claim 1;

(b) disrupting the cells to cause release of cellular components;

(c) causing the particles to be released from the vehicle; and (d) agitating the sample sufficiently such that nucleic acids are separated from other cellular components.

10. The method of claim 8 wherein the cells are disrupted by heating the sample at a temperature and for a time sufficient to render infectious organisms in the sample noninfectious.

11. The method of claim 8 wherein the particles are caused to be released from the vehicle by impact of a particle with the barrier.

* * * * *